United States Patent
Hsieh

(10) Patent No.: US 6,266,388 B1
(45) Date of Patent: Jul. 24, 2001

(54) METHODS AND APPARATUS FOR TWO-PASS CONE BEAM IMAGE RECONSTRUCTION

(75) Inventor: Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/390,448

(22) Filed: Sep. 7, 1999

(51) Int. Cl.⁷ .................................................. A61B 6/03
(52) U.S. Cl. ................... 378/8; 378/15; 378/901
(58) Field of Search ................ 378/4, 8, 15, 901

(56) References Cited

U.S. PATENT DOCUMENTS 5,960,056  * 9/1999  Lai .................................. 378/4

OTHER PUBLICATIONS

Feldkamp et al., "Practical cone–beam algorithm", J. Opt. Soc. Am. A., vol. 1, No. 6, pp. 612–619 (Jun. 1984).

* cited by examiner

*Primary Examiner*—David V. Bruce
(74) *Attorney, Agent, or Firm*—Armstrong Teasdale LLP; Christian G. Cabou

(57) ABSTRACT

The present invention, in one form, is a method for generating an image using data collected in a cone beam scan are described. In an exemplary embodiment, a method includes the steps of reconstructing an image ρ using the collected data, and segmenting image data for the image ρ into a plurality of data sets. At least one of the data sets corresponds to bone data. Then, an error image Ψ is generated by using the bone data image set, and a final corrected image χ is generated using ρ and the error only image Ψ.

20 Claims, 2 Drawing Sheets

METHODS AND APPARATUS FOR TWO-PASS CONE BEAM IMAGE RECONSTRUCTION

BACKGROUND OF THE INVENTION

This invention relates generally to computed tomography and, more particularly, to reconstructing an image using data collected in a scan using a computed tomography system.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two dimensional slice taken through the object. One method for reconstructing an image from a set of projection data is referred to in the art as the filtered back projection technique. This process converts the attenuation measurements from scan into integers called "CT numbers" or "Hounsfield units", which are used to control the brightness of a corresponding pixel on a cathode ray tube display.

Cone beam scanning is performed using a multi-dimensional detector array instead of a linear detector array as is used in a fan beam scan. In a cone beam helical scan, the x-ray source and the multi-dimensional detector array are rotated with a gantry within the imaging plane as the patient is moved in the z-axis synchronously with the rotation of the gantry. Such a system generates a multi-dimensional helix of projection data. As compared to fan beam helical scanning, cone beam helical scanning provides improved slice profiles, greater partial volume artifact reduction, and faster patient exam speed.

One known algorithm for performing image reconstruction using data collected in a cone beam scan is described in Feldkamp et al., "Practical cone-beam algorithm", J. Opt. Soc. Am. A., Vol. 1, No. 6, pp. 612–619, sometimes referred to herein as the Feldkamp algorithm. With the Feldkamp algorithm, and when objects with high density and non-uniform distribution are place off center plane (the fan beam plane), severe shading artifact may result.

BRIEF SUMMARY OF THE INVENTION

Methods and apparatus for generating an image using data collected in a cone beam scan are described. In an exemplary embodiment, a method includes the steps of reconstructing an initial image $\rho$ using the collected data, and segmenting image data for the image $\rho$ into a plurality of data sets. At least one of the data sets corresponds to high density objects. Then, an error image $\Psi$ is generated by using the high density image data set, and a final corrected image $\chi$ is generated using the initial image $\rho$ and error only image $\Psi$.

In the exemplary embodiment, the error image $\Psi$ is generated by generating a high density object image $\zeta$ using the high density image data set, and removing an original high density object image $\eta$ generated from the collected data from high. density object image $\zeta$. More specifically, the error image $\Psi$ is generated in accordance with:

$$\Psi = \zeta - f(\eta)$$

where f is a filtering function that estimates a point spread function of forward projection and reconstruction. The final corrected image $\chi$ is generated by removing error only image $\Psi$ from original image $\rho$ in accordance with:

$$\chi = \rho - g(\Psi)$$

where g is a filtering operator for noise reduction.

DETAILED DESCRIPTION OF THE INVENTION

Figure 1:
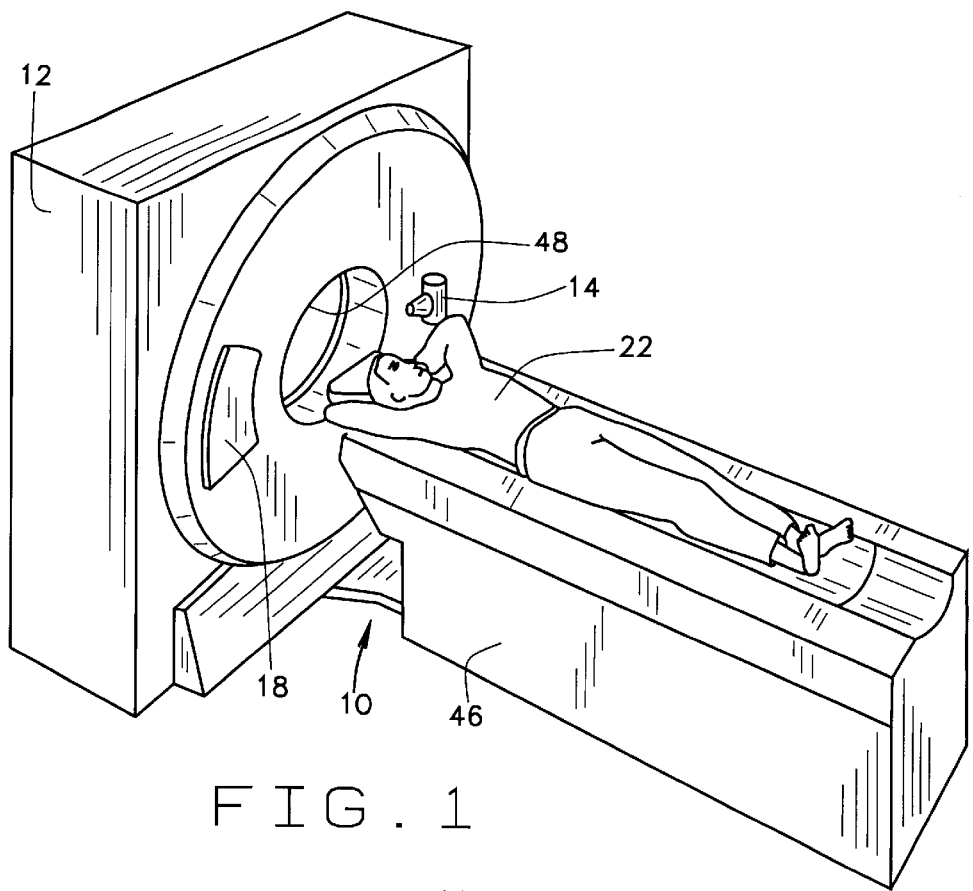
FIG. 1 is a pictorial view of a CT imaging system.
Figure 2:
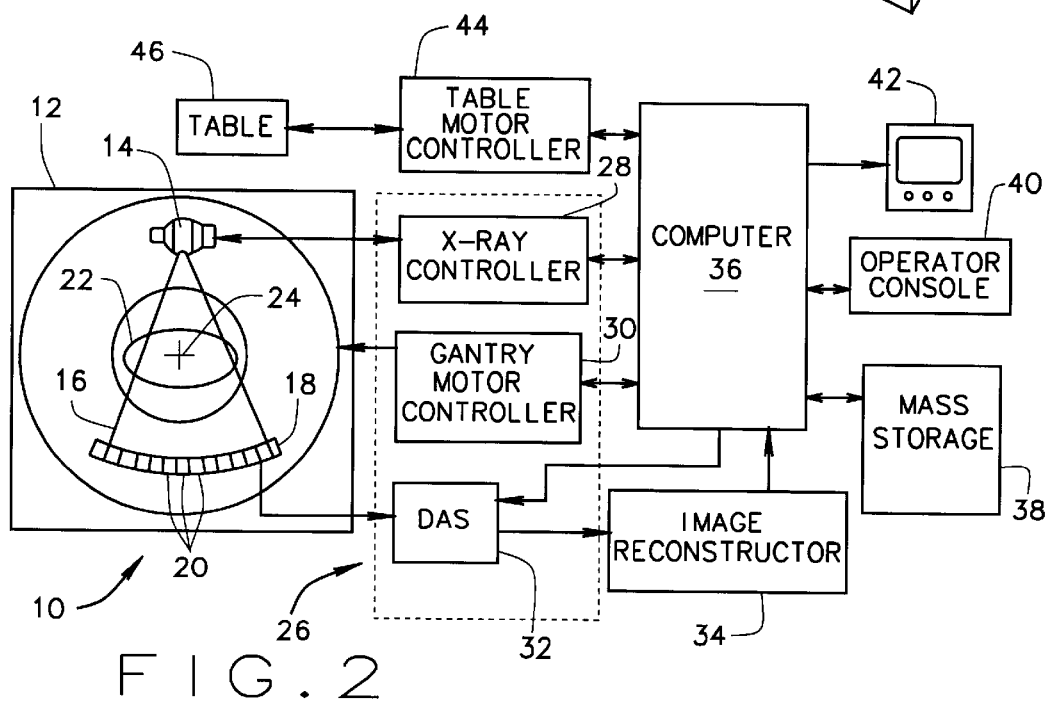
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object 22, for example a medical patient. Detector array 18 may be fabricated in a single slice or multi-slice configuration. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

The algorithms described below may be performed by a processor in image reconstructor 34. Such algorithms, however, may be performed by computer 36, or by another processor coupled to the system.

More specifically, and after performing a cone beam scan, an image ρ is reconstructed using a cone beam algorithm, such as the Feldkamp algorithm. The reconstructed image is then segmented into multiple classes, such as bone and soft tissue. Since there is a one to one correspondence between materials and the range of CT number, such classification could be performed using a simple threshold approach, e.g., if CT number is greater than 225, then classify as bone, otherwise classify as soft tissue. Of course, other more sophisticated methods can be used to perform the classification. The image data obtained as a result of such segmentation and that contain only bones (or other high density objects) is designated by η.

Then, error images are generated by first producing a set of "bone" projections based on η. Shading artifacts caused by cone beam reconstruction are generally low frequency in nature, and there is a smoothing effect in the forward projection. A new bone image, ζ, is obtained by reconstructing the bone projections with the same cone beam reconstruction algorithm used to generate ρ, such as the Feldkamp algorithm. The error only image, Ψ, is generated by removing the original bone image, η, from the new bone image, ζ:

$$\Psi = -f(\eta) \quad (1)$$

where f is a filtering function that estimates the point spread function (PSF) of the forward projection and reconstruction process. An exemplary filtering function is the Gaussian low pass filter, which is well known in the art.

Alternatively, an error only image Ψ could be generated by performing a segmentation on the new bone image, ζ, using a simple threshold approach, e.g., if CT number is greater than 225, then classify as bone, otherwise classify as error data. The bone data is then removed. As a result, Ψ contains only the artifacts caused by cone beam reconstruction.

The final corrected image, χ, is then obtained by removing error image, Ψ, from the original image, ρ:

$$\chi = \rho - g(\Psi) \quad (2)$$

where g is a filtering operator for further noise reduction. Again, cone beam artifacts are generally low frequency in nature. An example of a filtering operator is an exponential low pass filter or a median filter, which are well known in the art.

The above described method utilizes one forward cone beam projection and two cone beam reconstruction operations. The computational complexity of the method can be reduced. For example, the number of channels and number of views used for the forward projection and error reconstruction can be reduced. For example, if the original projection contains 400 detector channels and 400 detector rows, the forward projection can be performed using 200 detector channels and 200 rows. In the generated projections, each pixel is four times as large as the original projection (2 times in length and width). If the original projections contain 360 views, 200 views can be used for the forward projection generation. By reducing the number of views, significant (e.g., a factor greater than 7) computational reduction can be achieved.

Figure 3:
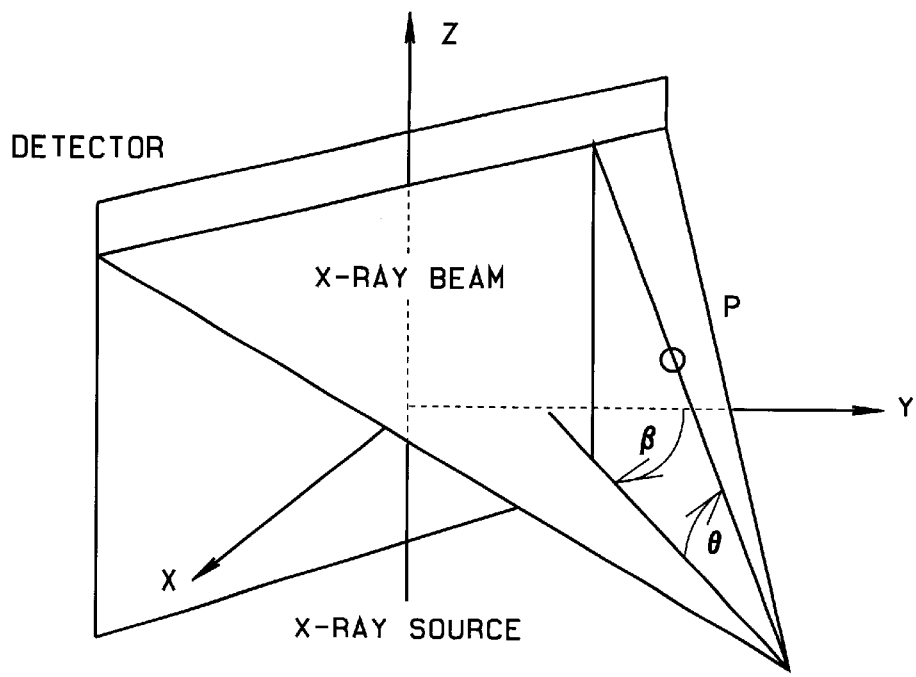
FIG. 3 illustrates a cone beam sampling geometry from an x-ray source.
Figure 4:
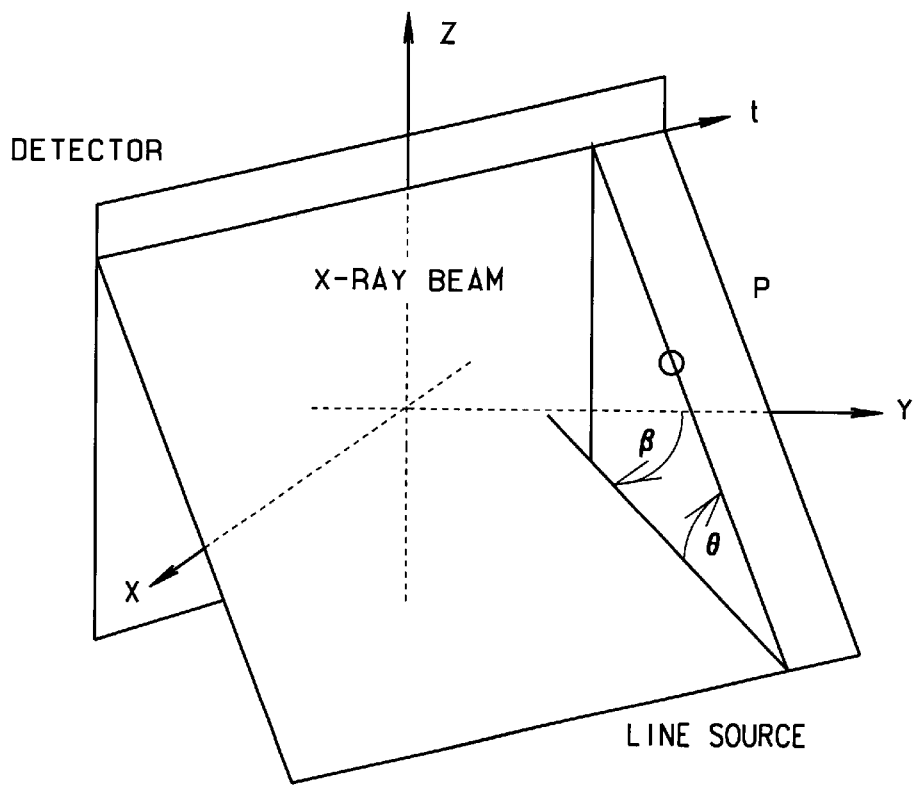
FIG. 4 illustrates a tilted parallel beam sampling geometry from a line source.

In addition, and to further reduce the amount of computation, a projection error estimation based on a tilted parallel beam geometry can be used. Similarly, the cone beam reconstruction algorithm is replaced with a tilted parallel beam reconstruction algorithm. To analyze the error caused by approximating the cone beam by the tilted parallel beam geometry in the cone beam error estimation, a point, P, inside the scan field in which the cone beam error needs to be estimated, is selected. A unique ray intersects each point P for each cone beam projection. Two angles to define the ray. The first angle, β, is the angle in the x-y plane formed with the y-axis by the plane passing through point P, containing the source, and parallel to the z-axis, as shown in FIG. 3. The second angle, θ, is the angle formed with the x-y plane by the ray passing through P. Using this notation, the angle β equals the projection angle only at the iso-ray (ray intersecting z-axis). Therefore, for the same projection angle α, the ray that intersects point P will be significantly different in the tilted parallel beam as shown in FIG. 4 than in cone beam geometry. As a result, the estimated beam path through the dense object will be in error.

However, by comparing the parallel projection whose projection angle is identical to angle β (since many views are generated, a view typically satisfies this condition), the difference in the parallel ray and the cone beam ray will be the tilt angle, θ. Since the geometry is rotational symmetric with respect to the z-axis, the point P can be selected to be a point in the x-z plane.

The angles $\theta_{cone}$ and $\theta_{tilt}$ denote the tilt angle for cone beam and the parallel beam, respectively. The difference tilt angle, $\Delta\theta$, for a point, P(x,z), can be expressed as:

$$\Delta\theta = \theta_{cone} - \theta_{tilt} \quad (3)$$

$$= \tan^{-1}\left[\frac{z}{\sqrt{x^2 + R^2 - 2x^2\cos^2\beta + 2x\sin\beta\sqrt{R^2 - x^2\cos^2\beta}}}\right] - \tan^{-1}\left[\frac{z}{R + x\sin\beta}\right]$$

where R is the x-ray source to iso-center distance. In general, this error increases with an increase in x and z.

Once the projection is generated by a set of tilted parallel beam projections from only the high density images, the error in the reconstructed image is estimated by reconstructing the projections. The derivation for the tilted parallel beam reconstruction is carried out in a similar fashion as the derivation used in the Feldkamp cone beam reconstruction algorithm. The resulting equation for the estimated error, e(x, y, z), is:

$$e(x, y, z) = \frac{1}{2}\int_0^{2\pi} \frac{d}{\sqrt{d^2 + Z^2}}\left[\int_{-\infty}^{\infty} S_\beta(\omega, z)|\omega|e^{j2\pi\omega t}d\omega\right]d\beta \quad (4)$$

where $$S_\beta(\omega, z) = \int_{-\infty}^{\infty} P_\beta(t, z)e^{-j\pi\omega t}dt \quad (5)$$

Point $P_\beta(t, z)$ is the projection intersecting the point (x, y, z).

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. In addition, the CT system described herein is a "third generation" system in which both the x-ray source and detector rotate with the gantry. Many other CT systems including "fourth generation" systems wherein the detector is a full-ring stationary detector and only the x-ray source rotates with the gantry, may be used if individual detector elements are corrected to provide substantially uniform responses to a given x-ray beam. Moreover, the system described herein performs an axial scan, however, the invention may be used with a helical scan although more than 360° of data are required. Accordingly, the spirit and scope of the invention are to be limited only by the terms of the appended claims.

What is claimed is:

1. A method for reconstructing an image using data collected in cone beam scan, said method comprising the steps of:

reconstructing an image ρ using the collected data;

segmenting image data for the image ρ into a plurality of data sets, at least one of the data sets corresponding to high density object data;

generating an error only image Ψ using the high density object data image set; and generating a final corrected image χ using the image ρ and the error only image Ψ.

2. A method in accordance with claim 1 wherein generating error only image Ψ comprises the steps of:

generating a high-density-object-plus-error image ζ using the high density object data image set; and removing from high-density-object-plus-error image ζ an original high density image η generated from the collected data.

3. A method in accordance with claim 2 wherein error only image is generated in accordance with:

$$\Psi = \zeta - f(\eta),$$

where f is a filtering function that estimates a point spread function of forward projection and reconstruction.

4. A method in accordance with claim 1 wherein segmenting image data for the image ρ into a plurality of data sets comprises the step of performing a thresholding operation on at least some of the collected data.

5. A method in accordance with claim 1 wherein at least one of the segmented data sets comprises soft tissue.

6. A method in accordance with claim 1 wherein generating the error only image Ψ comprises the steps of:

generating a high-density-object-plus-error image ζ using the high density object image data set; and segmenting a high-density-object-plus-error image ζ image data into a plurality of data sets, at least one of the data sets corresponding to error data.

7. A method in accordance with claim 1 wherein generating the final corrected image χ comprises the step of removing the error only image Ψ from the original image ρ in accordance with:

$$\chi = \rho - g(\Psi)$$

where g is a filtering operator for noise reduction.

8. A method in accordance with claim 2 wherein reconstructing an image ζ using the collected data is performed using less than all the collected data.

9. A method in accordance with claim 2 wherein reconstructing an image ζ using the collected data is performed using a tilted parallel beam reconstruction algorithm.

10. Apparatus for reconstructing an image using data collected in a cone beam scan, said apparatus comprising a processor programmed to:

reconstruct an image ρ using the collected data;

segment image data for the image ρ into a plurality of data sets, at least one of the data sets corresponding to high density object data;

generate an error only image Ψ using the high density object data image set; and generate a final corrected image χ using the image ρ and the error only image Ψ.

11. Apparatus in accordance with claim 10 wherein to generate error only image Ψ, said processor is programmed to:

generate a high-density-object-plus-error image ζ using the high density object image data set; and remove from high-density-plus-error image ζ an original high density image η generated from the collected data.

12. Apparatus in accordance with claim 11 wherein said processor is programmed to generate error only image Ψ in accordance with:

$$\Psi = \zeta - f(\eta),$$

where f is a filtering function that estimates a point spread function of forward projection and reconstruction.

13. Apparatus in accordance with claim 10 wherein to segment image data for the image ρ into a plurality of data sets, said processor is programmed to perform a thresholding operation on at least some of the collected data.

14. Apparatus in accordance with claim 10 wherein to generate the final corrected image χ, said processor is programmed to remove the error image Ψ from the original image ρ in accordance with:

$$\chi = \rho - g(\Psi)$$

where g is a filtering operator for noise reduction.

15. Apparatus in accordance with claim 11 wherein to reconstruct image ζ using the collected data, said processor is programmed to use less than all the collected data.

16. Apparatus in accordance with claim 11 wherein to reconstruct an image ζ using the collected data, said processor is programmed to use a tilted parallel beam reconstruction algorithm.

17. Apparatus for reconstructing an image using data collected in a cone beam scan, said apparatus comprising a processor programmed to:

reconstruct an image ρ using the collected data;

segment image data for the image ρ into a plurality of data sets, at least one of the data sets corresponding to high density object data;

generate an error only image Ψ using the high density object data image set by generating a high-density-object-plus-error image ζ using the high density object image data set; and then generating error only image Ψ in accordance with:

$$\Psi = \zeta - f(\eta),$$

where f is a filtering function that estimates a point spread function of forward projection and reconstruction; and generate a final corrected image χ in accordance with:

$$\chi = \rho - g(\Psi)$$

where g is a filtering operator for noise reduction.

18. Apparatus in accordance with claim 17 wherein to segment image data for the image $\rho$ into a plurality of data sets, said processor is programmed to perform a thresholding operation on at least some of the collected data.

19. Apparatus in accordance with claim 17 wherein to reconstruct image $\zeta$ using the collected data, said processor is programmed to use less than all the collected data.

20. Apparatus in accordance with claim 17 wherein to reconstruct an image $\zeta$ using the collected data, said processor is programmed to use a tilted parallel beam reconstruction algorithm.

\* \* \* \* \*

UNITED STATES PATENT AND TRADEMARK OFFICE
CERTIFICATE OF CORRECTION

PATENT NO. : 6,266,388 B1
DATED : July 24, 2001
INVENTOR(S) : Hsieh

It is certified that error appears in the above-identified patent and that said Letters Patent is hereby corrected as shown below:

Column 1,
Line 38, delete "from scan" and subtitute -- from a scan --.

Column 2,
Line 9, delete "high." substitute -- high --.

Column 3,
Line 35, delete "$\Psi=-f(\eta)$" and substitute -- $\Psi=\zeta-f(\eta)$ --.

Column 6,
Line 18, delete "high-density-plus-error" and substitute -- high-density-object-plus-error --.

Signed and Sealed this

First Day of October, 2002

*Attest:*

JAMES E. ROGAN
*Attesting Officer*     *Director of the United States Patent and Trademark Office*